US011486007B2

(12) United States Patent
Pedersen et al.

(10) Patent No.: US 11,486,007 B2
(45) Date of Patent: Nov. 1, 2022

(54) METHYLATED MARKERS FOR COLORECTAL CANCER

(71) Applicants: Quest Diagnostics Investments Incorporated, Wilmington, DE (US); CLINICAL GENOMICS PTY LTD, North Ryde (AU)

(72) Inventors: Susanne Pedersen, North Ryde (AU); Lawrence LaPointe, Edison, NJ (US); Rohan Baker, North Ryde (AU); Amber C. Donahue, Rancho Santa Margarita, CA (US); Yen-lin Peng, Mission Viejo, CA (US); Frederic Waldman, San Juan Capistrano, CA (US)

(73) Assignees: Quest Diagnostics Investments Incorporated, Wilmington, DE (US); CLINICAL GENOMICS PTY LTD, North Ryde (AU)

( * ) Notice: Subject to any disclaimer, the term of this patent is extended or adjusted under 35 U.S.C. 154(b) by 82 days.

(21) Appl. No.: 15/315,874

(22) PCT Filed: Jun. 3, 2015

(86) PCT No.: PCT/US2015/033968
§ 371 (c)(1),
(2) Date: Dec. 2, 2016

(87) PCT Pub. No.: WO2015/187823
PCT Pub. Date: Dec. 10, 2015

(65) Prior Publication Data
US 2017/0191135 A1    Jul. 6, 2017

Related U.S. Application Data

(60) Provisional application No. 62/007,687, filed on Jun. 4, 2014.

(51) Int. Cl.
*C12Q 1/68* (2018.01)
*C12P 19/34* (2006.01)
*C12Q 1/6886* (2018.01)

(52) U.S. Cl.
CPC ...... *C12Q 1/6886* (2013.01); *C12Q 2600/118* (2013.01); *C12Q 2600/154* (2013.01); *C12Q 2600/158* (2013.01)

(58) Field of Classification Search
CPC combination set(s) only.
See application file for complete search history.

(56) References Cited

U.S. PATENT DOCUMENTS

| 2006/0051768 | A1 | 3/2006 | Hoon |
| 2009/0317810 | A1 | 12/2009 | Lofton-Day et al. |
| 2010/0143902 | A1* | 6/2010 | Lofton-Day ......... C12Q 1/6886 435/6.14 |

FOREIGN PATENT DOCUMENTS

| JP | 2009-533066 A | 9/2009 |
| WO | WO-2007/118704 A2 | 10/2007 |
| WO | WO-2012/034170 A1 | 3/2012 |
| WO | WO 2013/166558 A1 | 11/2013 |
| WO | WO-2013/170314 A1 | 11/2013 |

OTHER PUBLICATIONS

New England Biolabs 1998/99 catalog, "Random Primers" p. 121 and p. 284 (Year: 1998).*
Oster, B. et al. Int. J. Cancer: 132, 2303-2315, published online Nov. 1, 2012. (Year: 2012).*
Baker, R. et al. "Clinical evaluation of a novel 2-gene methylation blood test for colorectal cancer" Abstract—Journal of Gastroenterology and Hepatology 2012; 27 (Suppl. 4): 123-124. (Year: 2012).*
Baker, R. et al. "Clinical evaluation of a novel 2-gene methylation blood test for colorectal cancer" POSTER #186/ ID 1408542—Australian Gastroenterology Week 2012. Oct. 16-19, 2012. Adelaide, South Australia, Australia (Year: 2012).*
*Homo sapiens* chromosome 7, GRCh37.p10 Primary Assembly, Oct. 30, 2012, human chromosome 7 showing 27.98kb region from base 50,341,378 to 50,369,358, pp. 1-19 printed from https://www.ncbi.nlm.nih.gov. (Year: 2012).*
Brenner, D.E. et al. "Fecal DNA Biomarkers for the Detection of Colorectal Neoplasia: Attractive, but Is It Feasible?" Journal of the National Cancer Institute, vol. 97, No. 15, pp. 1107-1108, Aug. 3, (Year: 2005).*
Zhang, W. et al. "Predicting genome-wide DNA methylation using methylation marks, genomic position, and DNA regulatory elements" Zhang et al. Genome Biology (2015) 16:14 (Year: 2015).*
Costello, J.F. et al. "Graded Methylation in the Promoter and Body of the 06-Methylguanine DNA Methyltransferase (MGMT) Gene Correlates with MGMT Expression in Human Glioma Cells" The Journal of Biological Chemistry, vol. 269, No. 25, Issue of Jun. 24, pp. 17228-17237. (Year: 1994).*
International Search Report dated Dec. 7, 2015 in application No. PCT/US2015/33968.
DATABASE Geneseq [Online], "BCAT1 gene methylation specific reverse PCR primer"; XP055428163; Database Accession No. BAY70260; Jan. 16, 2014, 1 page.
DATABASE Geneseq [Online], "BCAT1 methylation specific forward PCR primer"; XP055428160; Database Accession No. BAY70259; Jan. 16, 2014, 1 page.
DATABASE Geneseq [Online], "Human BCAT1 genomic DNA specific probe"; XP055428164; Database Accession No. BAY52313; Jan. 2, 2014, 1 page.
DATABASE Geneseq [Online], "IKZF1 gene methylation specific reverse PCR primer"; XP055428155; Database Accession No. BAY70263; Jan. 16, 2014, 1 page.

(Continued)

*Primary Examiner* — Stephen T Kapushoc
(74) *Attorney, Agent, or Firm* — Foley & Lardner LLP

(57) ABSTRACT

Disclosed herein is a combination of genomic sequences whose methylation patterns have utility for the improved detection and differentiation between colorectal neoplasms. Further disclosed herein are methods, nucleic acids and kits for detecting or differentiating between colorectal neoplasms.

8 Claims, 5 Drawing Sheets
Specification includes a Sequence Listing.

(56) References Cited

OTHER PUBLICATIONS

Extended European Search Report dated Dec. 1, 2017 as issued in corresponding European Application No. 15803889.3.
Mitchell et al.: "A Panel of Genes Methylated with High Frequency in Colorectal Cancer", BMC Cancer, Biomed Central, vol. 14, No. 1, Jan. 31, 2014, p. 54, XP021175595.
Young et al.: "Evaluation of a 2-Gene (IKZF1 and BCAT1) DNA Blood Test for Detection of Colorectal Cancer", Gastroenterology, vol. 146, No. 5, Suppl. 1, May 2014, pp. S56-S57, XP009501828.
Japanese Office Action dated Apr. 16, 2019 as issued in corresponding Japanese Application No. 2017-516255 and its English translation thereof.

* cited by examiner

|  | Cases (n=198) | | Controls (n=94) | | |
|---|---|---|---|---|---|
|  | Positive (true pos #) | Sensitivity (%) | Positive (false pos #) | False pos rate (%) | Specificity (%) |
| Septin 9 | 135 | 68 | 5 | 5 | 95 |
| IKZF1 | 112 | 57 | 7 | 7 | 93 |
| BCAT1 | 112 | 57 | 4 | 4 | 96 |
| S9 &/or IKZ | 148 | 75 | 11 | 12 | 88 |
| S9 &/or BCAT | 143 | 72 | 7 | 7 | 93 |
| IKZ &/or BCAT | 133 | 67 | 10 | 11 | 89 |
| Triplex (any pos marker) | 155 | 78 | 13 | 14 | 86 |

FIGURE 1

|  | Stage I (n=25) | Stage II (n=74) | Stage III (n=62) | Stage IV (n=36) |
|---|---|---|---|---|
|  | # detected (%) | # detected (%) | # detected (%) | # detected (%) |
| Septin 9 | 16 (64) | 43 (58) | 43 (69) | 33 (92) |
| IKZF1 | 11 (44) | 38 (51) | 34 (55) | 29 (81) |
| BCAT1 | 9 (36) | 41 (55) | 32 (52) | 30 (83) |
| S9 &/or IKZ | 17 (68) | 50 (68) | 48 (77) | 33 (92) |
| S9 &/or BCAT | 16 (64) | 50 (68) | 44 (71) | 33 (92) |
| IKZ &/or BCAT | 12 (48) | 49 (66) | 40 (65) | 32 (89) |
| Triplex (any pos marker) | 17 (68) | 56 (76) | 49 (79) | 33 (92) |
| Additional cases detected by addition of new markers | 1 | 13 | 6 | 0 |

FIGURE 2

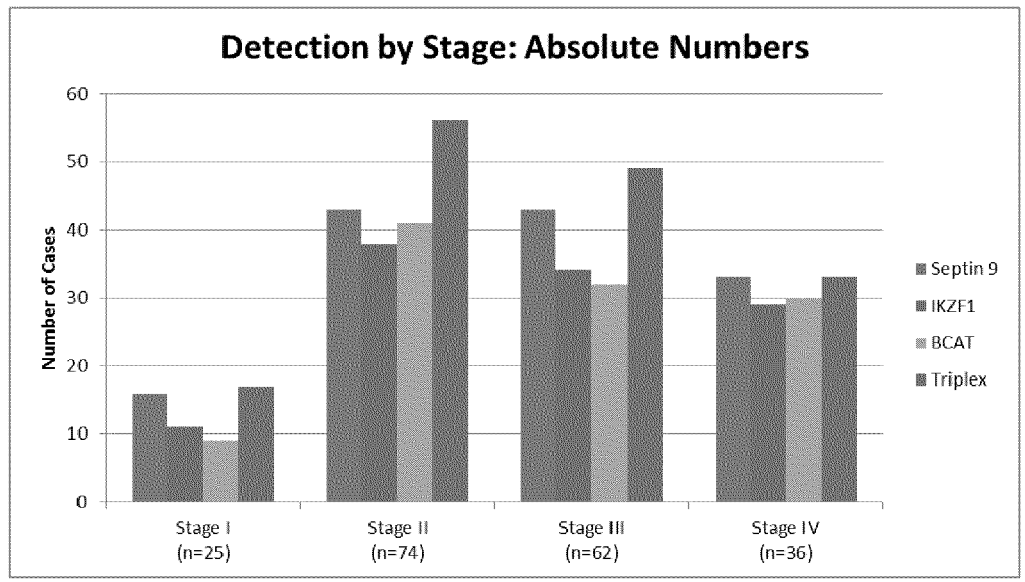
FIGURE 3A
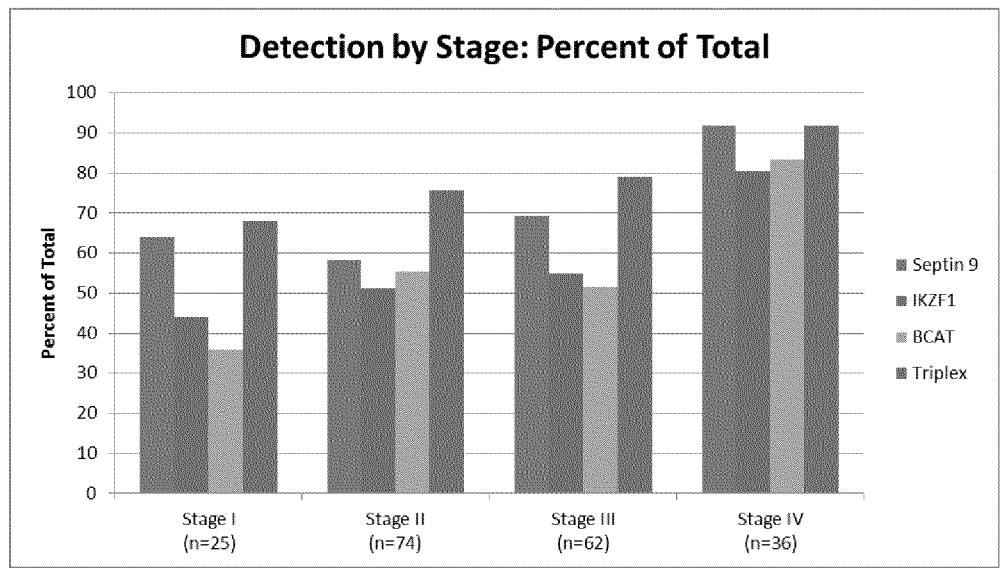
FIGURE 3B
FIGURE 3

|  | Sensitivity | | | Specificity | | |
|---|---|---|---|---|---|---|
|  | ≥1 well = POS | ≥2 well = POS | 3 well = POS | ≥1 well = POS | ≥2 well = POS | 3 well = POS |
|  | % (#TP) | % (#TP) | % (#TP) | % (#FP) | % (#FP) | % (#FP) |
| Septin 9 | 68 (135) | 51 (100) | 42 (84) | 95 (5) | 97 (3) | 98 (2) |
| IKZF1 | 57 (112) | 44 (87) | 37 (73) | 93 (7) | 99 (1) | 99 (1) |
| BCAT1 | 57 (112) | 43 (86) | 33 (66) | 96 (4) | 98 (2) | 98 (2) |
| S9 &/or IKZ | 75 (148) | 56 (110) | 47 (93) | 88 (11) | 97 (3) | 98 (2) |
| S9 &/or BCAT | 72 (143) | 55 (108) | 44 (87) | 93 (7) | 97 (3) | 98 (2) |
| IKZ &/or BCAT | 67 (133) | 52 (102) | 42 (84) | 89 (10) | 98 (2) | 98 (2) |
| Triplex (any pos marker) | 78 (155) | 58 (114) | 48 (94) | 86 (13) | 97 (3) | 98 (2) |

FIGURE 4

| | PRESEPT Clinical Trial (Feb 2010)a | Prospective Screening Study Pivotal Clinical Trial for FDA Submission (Dec 2011)b | Epi ProColon Comparison to Automated FIT Study for FDA Submission (Dec 2012)b | CHA ColoVantage v1.0 Validation Study (~May 2011)c | SJC ColoVantage "v2.0" Pilot Study (March 2014): Septin 9 only | SJC ColoVantage "v2.0" Pilot Study (March 2014): Triplex |
|---|---|---|---|---|---|---|
| Samples | 79401 (actually tested 1478) | 15441 | 2901 | 2521 | 2922 | 2922 |
| Sensitivity | 67% | 68% | 72% | 70% | 68% | 78% |
| Specificity | 88% | 79% | 81% | 89% | 95% | 86% |
| Assay/Kit | First-generation Epi ProColon | Current Epi proColon | Current Epi proColon | ColoVantage "v1.0" (based on first-generation Epi ProColon) | ColoVantage "v2.0" (Septin 9 redesign) | ColoVantage "v2.0" (S9/IKZ/BCAT redesigns) |

[1] Controls = age-restricted & colonoscopy-negative
[2] Normals = no age restriction & colonoscopy status unknown

[a] Church et al. Prospective evaluation of methylated *SEPT9* in plasma for detection of asymptomatic colorectal cancer. *Gut* 2014;63:317-325
[b] Epi ProColon Test Product Summary and Briefing Packet (FDA submission):
http://www.fda.gov/downloads/AdvisoryCommittees/CommitteesMeetingMaterials/MedicalDevices/MedicalDevicesAdvisoryCommittee/MolecularandClinicalGeneticsPanel/UCM390234.pdf
[c] Nichols Institute-Chantilly Validation Report #CHA MG.V50, "Laboratory Developed Test of Plasma Septin 9 DNA Methylation for Colorectal Cancer Detection"

FIGURE 5

METHYLATED MARKERS FOR COLORECTAL CANCER

CROSS-REFERENCE TO RELATED APPLICATIONS

This application claims the benefit of U.S. Provisional application No. 62/007,687 filed Jun. 4, 2014, the contents of which are incorporated herein by reference in their entirety.

BACKGROUND OF THE INVENTION

Colorectal cancer (CRC) is the third most common form of cancer and the second leading cause of cancer-related deaths in the western world. Its natural evolution (adenoma-carcinoma sequence is believed to occur in most patients) and accessibility by non-surgical methods makes it suitable for early detection and prevention.

Early detection greatly improves the chances of curing CRC. Colonoscopy is an extremely specific and sensitive test, however, it is an invasive test which requires bowel preparation and patient cooperation. It is also associated with a minor risk of serious complications, reducing its generalized use. There exists a need for non-invasive detection of pre-malignant and malignant neoplastic alterations of the colon with high sensitivity and excellent specificity.

SUMMARY OF THE INVENTION

Disclosed herein, in some embodiments, is a method of screening for a colorectal neoplasm or predisposition for developing a colorectal neoplasm in a subject, comprising: assaying a biological sample from the subject by determining the methylation state of the Septin 9 gene and the methylation state of one additional marker gene within the biological sample, wherein the one additional marker gene is selected from the Ikaros family zinc-finger 1 (IKZF1) gene and the branched-chain aminotransferase 1 (BCAT1) gene, wherein methylation of Septin 9 and the one additional marker gene is indicative of a colorectal neoplasm, or predisposition for developing a colorectal neoplasm, in the subject. In some embodiments, assaying a biological sample comprises determining the methylation state of the Septin 9 gene, the IKZF1 gene, and the BCAT1 gene. In some embodiments, determining the methylation state of the Septin 9 gene and the methylation state of one additional marker gene comprises at least one of amplification, PCR method, isothermal amplification, NASBA method, LCR method, methylation specific amplification, Methylation Specific PCR (MSP), nested MSP, Heavy-Methyl™, bisulfite sequencing, detection by means of DNA-arrays, detection by means of oligo-nucleotide microarrays, detection by means of CpG-island-microarrays, detection by means of restriction enzymes, the COBRA method, real-time PCR, HeavyMethyl™ real time PCR, MSP MethyLight™, MethyLight™ Algo™, the QM method, Headloop MethyLight™, HeavyMethyl™ MethyLight™, HeavyMethyl™ Scorpion™, MSP Scorpion™, Headloop Scorpion™ method, methylation sensitive primer extension, and MS-SNuPE (Methylation-Sensitive Single Nucleotide Primer Extension). In some embodiments, the biological sample is a blood or plasma sample. In some embodiments, the biological sample is a stool sample, enema wash, surgical section or tissue biopsy. In some embodiments, the neoplasm is a cancer. In some embodiments, the neoplasm is an adenoma. In some embodiments, the neoplasm is pre-cancerous. In some embodiments, said subject is human. In some embodiments, the biological sample comprises genomic DNA. In some embodiments, the biological sample comprises cell free DNA.

Disclosed herein, in some embodiments, is a method for methylation analysis of DNA, comprising: a) treating DNA from a biological sample with one or more reagents capable of converting unmethylated cytosine bases to uracil sulfonate or to another base having a different binding behavior than cytosine while leaving methylated cytosine unaffected; and b) amplifying the treated DNA by means of: i) a primer specific for a Septin 9 gene; ii) a primer specific for an IZKF1 or a BCAT1 gene; and c) detecting the amplified DNA. In some embodiments, the method comprises amplifying the treated by means of: i) a primer specific for a Septin 9 gene; ii) a primer specific for an IZKF1 gene; and iii) a primer specific for a BCAT1 gene.

In some embodiments, disclosed herein is a method for methylation analysis of DNA, comprising: a) treating DNA from a biological sample with one or more reagents capable of converting unmethylated cytosine bases to uracil sulfonate; and b) amplifying the treated DNA by means of: i) a pair of oligonucleotides comprising or consisting of SEQ ID NOs: 1 and 2; and variants thereof; ii) a pair of oligonucleotides comprising or consisting of SEQ ID NOs: 4 and 5, and variants thereof; or a pair of oligonucleotides comprising or consisting of SEQ ID NOs: 7 and 8, and variants thereof; and iii) optionally an oligonucleotide selected from SEQ ID NO:3, SEQ ID NO:6, and SEQ ID NO:9 and variants thereof; and c) detecting the amplified DNA.

In some embodiments, disclosed herein is an oligonucleotide composition comprising or consisting essentially of: i) a pair of oligonucleotides comprising or consisting of SEQ ID NOs: 1 and 2; and variants thereof; ii) a pair of oligonucleotides comprising or consisting of: 1) SEQ ID NOs: 4 and 5, and variants thereof; or 2) SEQ ID NOs: 7 and 8, and variants thereof; and iii) optionally an oligonucleotide selected from SEQ ID NO:3, SEQ ID NO:6, SEQ ID NO:9 and combinations thereof. In some embodiments, the oligonucleotide composition comprises a pair of oligonucleotides comprising or consisting of SEQ ID NOs: 4 and 5, and variants thereof; and a pair of nucleotides comprising or consisting of SEQ ID NOs: 7 and 8, and variants thereof.

BRIEF DESCRIPTION OF THE DRAWINGS

FIG. 1 exemplifies sensitivity and specificity of Septin 9, IKZF1, and BCAT1 methylation markers, alone and in combination. The addition of IKZF1 and BCAT1 to Septin 9 resulted in the capture of 20 additional cases (sensitivity increase of 10%).

FIG. 2 exemplifies the sensitivity of the Septin 9, IKZF1, and BCAT1 methylation markers, alone or in combination, by colorectal cancer stage. Addition of IKZF1 and BCAT1 to Septin 9 captured an additional 13 stage II cases and 6 stage III cases, improving detection of earlier stage cancers.

FIG. 3 exemplifies sensitivity of the Septin 9, IKZF1, and BCAT1 methylation markers, alone or in combination, in detecting colorectal cancer by stage in absolute number (3A) and by percent of total (3B).

FIG. 4 exemplifies sensitivity and specificity of Septin 9, IKZF1, and BCAT1 methylation markers, alone and in combination in detecting colorectal cancer using ≥1 well, ≥2 wells, and ≥3 wells.

FIG. 5 exemplifies differences in performance between various protocols in detecting colorectal cancer.

DETAILED DESCRIPTION OF THE INVENTION

Described herein are method, primers, reagents and kits for detection of a colorectal neoplasm.

To facilitate an understanding of the present disclosure, a number of terms and phrases are defined below.

As used herein, unless indicated otherwise, when referring to a numerical value, the term "about" means plus or minus 10% of the enumerated value.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplification product," also known as an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp. 13-20; Wharam et al., Nucleic Acids Res., 29(11):E54-E54, 2001; Hafner et al., Biotechniques, 30(4):852-56, 858, 860, 2001; Zhong et al., Biotechniques, 30(4):852-6, 858, 860, 2001.

As used herein, the term "oligonucleotide" or "polynucleotide" refers to a short polymer composed of deoxyribonucleotides, ribonucleotides, or any combination thereof. Oligonucleotides are generally between about 10, 11, 12, 13, 14, 15, 20, 25, or 30 to about 150 nucleotides (nt) in length, more preferably about 10, 11, 12, 13, 14, 15, 20, 25, or 30 to about 70 nt.

As used herein, a "primer" is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal extension and/or amplification. The term "primer" includes all forms of primers that may be synthesized including peptide nucleic acid primers, locked nucleic acid (LNA) primers, phosphorothioate modified primers, labeled primers, and the like. As used herein, a "forward primer" is a primer that is complementary to the anti-sense strand of DNA. A "reverse primer" is complementary to the sense-strand of DNA.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the $T_m$ of the formed hybrid.

As used herein, an oligonucleotide is "specific" for a nucleic acid if it is capable of hybridizing to the target of interest and not substantially hybridizing to nucleic acids which are not of interest. High levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art (e.g., BLAST).

As used herein, a "variant" of an oligonucleotide (such as an oligonucleotide probe or primer) has a similar length to a particular oligonucleotide (within 5 nucleotides) and hybridizes to substantially the same region as the particular oligonucleotide. In one embodiment, the variant oligonucleotide hybridizes under stringent conditions to a particular oligonucleotide. Stringent hybridization conditions generally include a relatively high annealing temperature (e.g. ~60-63° C.), which will favor the binding of the variant oligonucleotide to its target, and will lead to dissociation of the variant oligonucleotide from any off-target sequence to which it may have briefly bound.

The term "region of interest" refers to a region of a nucleic acid to be sequenced.

The term "biological sample" as used herein refers to a sample containing nucleic acids of interest. A biological sample may comprise clinical samples (i.e., obtained directly from a patient) or isolated nucleic acids and may be cellular or acellular fluids and/or tissue (e.g., biopsy) samples. In some embodiments, a sample is obtained from a tissue or bodily fluid collected from a subject. Sample sources include, but are not limited to, sputum (processed or unprocessed), bronchial alveolar lavage (BAL), bronchial wash (BW), whole blood or isolated blood cells of any type (e.g., lymphocytes), bodily fluids, cerebrospinal fluid (CSF), urine, plasma, serum, or tissue (e.g., biopsy material). Methods of obtaining test samples and reference samples are well known to those of skill in the art and include, but are not limited to, aspirations, tissue sections, drawing of blood or other fluids, surgical or needle biopsies, collection of paraffin embedded tissue, collection of body fluids, collection of stool, and the like. In the present context the biological sample preferably is blood, serum or plasma.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who possesses, or is suspected to possess, a genetic polymorphism of interest.

As used herein, the terms "stage I cancer," "stage II cancer," "stage III cancer," and "stage IV" refer to the TNM staging classification for cancer. Stage I cancer typically identifies that the primary tumor is limited to the organ of origin. Stage II intends that the tumor has spread through the muscle wall of the colon. Stage III intends that the tumor has spread to lymph nodes. Stage IV intends that the primary tumor has spread to other organs.

As used herein, "methylation status" refers to the level of methylation of cytosine residues (found in CpG pairs) in the gene of interest. When used in reference to a CpG site, the methylation status may be methylated or unmethylated. The levels of methylation of a gene of interest are determined by any suitable means.

Methylation Analysis

Disclosed herein, in some embodiments, is a method of screening for a colorectal neoplasm or predisposition for developing a colorectal neoplasm in a subject, comprising: assaying a biological sample from the subject by determining the methylation state of the Septin 9 gene and the methylation state of one additional marker gene within the biological sample, wherein the one additional marker gene is selected from the Ikaros family zinc-finger 1 (IKZF1) gene and the branched-chain aminotransferase 1 (BCAT1) gene, wherein methylation of Septin 9 and the one additional marker gene is indicative of a colorectal neoplasm, or predisposition for developing a colorectal neoplasm, in the subject. In some embodiments, assaying a biological sample comprises determining the methylation state of the Septin 9 gene, the IKZF1 gene, and the BCAT1 gene.

Disclosed herein, in some embodiments, is a method for methylation analysis of DNA, comprising: a) treating DNA from a biological sample with one or more reagents capable of converting unmethylated cytosine bases to uracil sulfonate or to another base having a different binding behavior than cytosine while leaving methylated cytosine unaffected; and b) amplifying the treated DNA by means of: i) a primer specific for a Septin 9 gene; ii) a primer specific for an IZKF1 or a BCAT1 gene; and c) detecting the amplified DNA. In some embodiments, the method comprises amplifying the treated by means of: i) a primer specific for a Septin 9 gene; ii) a primer specific for an IZKF1 gene; and iii) a primer specific for a BCAT1 gene.

Septin 9

The human Septin 9 gene (also known as MLL septin-like fusion protein, MLL septin-like fusion protein MSF-A, Sipa, Eseptin, Msf, septin-like protein Ovarian/Breast septin (Ov/Br septin) and Septin D1) is a member of the Septin gene family. Members of the Septin gene family have been thought to be associated with multiple cellular functions ranging from vesicle transport to cytokinesis. The Septin 9 gene is known to comprise four transcript variants, the Septin 9 variants and the Q9HC74 variants (which are truncated versions of the Septin 9 transcripts). The Septin 9 and Q9HC74 transcripts each comprise a CpG rich promotor region, respectively. Disruption of the action of Septin 9 results in incomplete cell division, and Septin 9 has been shown to be fusion partners of the protooncogene MLL suggesting a role in tumorigenesis.

IZKF1

The human Ikaros family zinc finger protein 1 (IZKF1) gene, is also known as the gene encoding DNA-binding protein Ikaros. The IZKF1 protein has been found to be a major tumor suppressor and the loss of its function has been linked to lymphoid leukemia. IKZF1 is known to be upregulated in granulocytes, B cells T cells and natural killer cells, and downregulated in erythroblasts, megakaryocytes and monocytes.

BCAT1

The human branched chain aminotransferase 1 (BCAT1) gene encodes the enzyme responsible for catalyzing the first step in the metabolism of branched-chain amino acids such as leucine, isoleucine and valine. BCAT1 has limited expression and is thought to be found only in certain tissues, such as embryonic tissues, in adult brain, ovary, and placenta. Expression of the BCAT1 gene has been associated with proliferation in yeast and increased metastatic potential in human cancers.

In some embodiments, additional genes are analyzed for methylation status. In some embodiments, an additional gene selected from IRF4, GRASP, CAHM, VIM1, TMEFF2, SOX21, SLC5A15, NPY. ST8SIA1, ZSCAN18, COL4A2, DLX5, FGF5, FOXF1, FOXI2, and SDC2 is analyzed for methylation status.

In some embodiments, disclosed herein is a method for methylation analysis of DNA, comprising: a) treating DNA from a biological sample with one or more reagents capable of converting unmethylated cytosine bases to uracil sulfonate; and b) amplifying the treated DNA by means of: i) a pair of oligonucleotides comprising or consisting of SEQ ID NOs: 1 and 2; and variants thereof; ii) a pair of oligonucleotides comprising or consisting of SEQ ID NOs: 4 and 5, and variants thereof; or a pair of oligonucleotides comprising or consisting of SEQ ID NOs: 7 and 8, and variants thereof; and iii) optionally an oligonucleotide selected from SEQ ID NO:3, SEQ ID NO:6, and SEQ ID NO:9 and variants thereof; and c) detecting the amplified DNA.

In some embodiments, disclosed herein is an oligonucleotide composition comprising or consisting essentially of: i) a pair of oligonucleotides comprising or consisting of SEQ ID NOs: 1 and 2; and variants thereof; ii) a pair of oligonucleotides comprising or consisting of: 1) SEQ ID NOs: 4 and 5, and variants thereof; or 2) SEQ ID NOs: 7 and 8, and variants thereof; and iii) optionally an oligonucleotide selected from SEQ ID NO:3, SEQ ID NO:6, SEQ ID NO:9 and combinations thereof. In some embodiments, the oligonucleotide composition comprises a pair of oligonucleotides comprising or consisting of SEQ ID NOs: 4 and 5, and variants thereof; and a pair of nucleotides comprising or consisting of SEQ ID NOs: 7 and 8, and variants thereof.

In some embodiments, the methods disclosed herein are useful in the detection of a colorectal neoplasm. In some embodiments, the colorectal neoplasm is premalignant. In some embodiments, the colorectal neoplasm is malignant. In some embodiments, the colorectal neoplasm is colorectal cancer without regard to stage of the cancer (e.g., stage I, II, III, or IV). In some embodiments, the colorectal cancer is a stage I cancer. In some embodiments, the colorectal cancer is a stage II cancer. In some embodiments, the colorectal cancer is a stage III cancer. In some embodiments, the colorectal cancer is a stage IV cancer. In some embodiments, the colorectal neoplasm is adenoma, without regard to the size of the adenoma (e.g., greater than 3 cm; less than or equal to 3 cm; greater than 1 cm; less than or equal to 1 cm). In some embodiments, the adenoma is considered to be an advanced adenoma.

In some embodiments wherein a colorectal neoplasm is detected, additional techniques are performed to characterize the colorectal neoplasm (e.g., to characterize the colorectal neoplasm as malignant or premalignant) (e.g., to characterize the colorectal neoplasm within a particular stage of colorectal cancer).

In some embodiments, the present invention provides methods for monitoring methylation status over time. For example, in some embodiments, the methods may be performed monthly, every six months, yearly, every 2 years, every 3 years, every 4 years, every 5 years, or longer time interval.

In some embodiments, the present invention provides methods for monitoring treatment of a colorectal neoplasm. For example, in some embodiments, the methods may be performed immediately before, during and/or after a treatment to monitor treatment success. In some embodiments, the methods are performed at intervals on disease-free patients to ensure or monitor treatment success.

In some embodiments, the present invention provides methods for obtaining a subject's risk profile for developing a colorectal neoplasm.

In some embodiments, the biological sample is a blood or plasma sample. In some embodiments, the biological sample is a stool sample, enema wash, surgical section or tissue biopsy. In some embodiments, the neoplasm is a cancer. In some embodiments, the neoplasm is an adenoma. In some embodiments, the neoplasm is pre-cancerous. In some embodiments, said subject is human. In some embodiments, the biological sample comprises genomic DNA. In some embodiments, the biological sample comprises cell free DNA.

Methods for Detection of Methylation

In some embodiments, determining the methylation state of the Septin 9 gene and the methylation state of one additional marker gene is performed by any suitable method. A number of methods are available for detection of differentially methylated DNA at specific loci in either primary tissue samples or in patient samples such as blood, urine, stool or saliva (reviewed in Kristensen and Hansen *Clin Chem.* 55: 1471-83, 2009; Ammerpohl et al. *Biochim Biophys Acta.* 1790:847-62, 2009; Shames et al. *Cancer Lett.* 251: 187-98, 2007; Clark et al. *Nat Protoc.* 1:2353-64, 2006). In some embodiments, methylation status analysis is accomplished by at least one of amplification, PCR method, isothermal amplification, NASBA method, LCR method, methylation specific amplification, Methylation Specific PCR (MSP), nested MSP, Heavy-Methyl™, bisulfite sequencing, detection by means of DNA-arrays, detection by means of oligonucleotide microarrays, detection by means of CpG-island-microarrays, detection by means of restriction enzymes, the COBRA method, real-time PCR, HeavyMethyl™ real time PCR, MSP MethyLight™, MethyLight™ Algo™, the QM method, Headloop MethyLight™, HeavyMethyl™ MethyLight™, HeavyMethyl™ Scorpion™, MSP Scorpion™, Headloop Scorpion™ method, methylation sensitive primer extension, and MS-SNuPE (Methylation-Sensitive Single Nucleotide Primer Extension). Additional techniques used to assess DNA methylation levels include, Restriction Landmark Genomic Scanning for Methylation (RLGS-M), comprehensive high-throughput relative methylation (CHARM) analysis, methylated DNA immunopreciptiation, methylation specific restriction enzyme analysis, and quantitative bisulfite pyrosequencing. (See, e.g. PCT Pub. No. WO2012/034170, which is incorporated by reference in its entirety)

In certain embodiments, the present invention provides kits for detecting the presence of a colorectal neoplasm. In some embodiments, such kits include reagents useful, sufficient, or necessary for detecting and/or characterizing one or more methylated marker genes specific for a colorectal neoplasm, as disclosed herein. In some embodiments, the kits contain the reagents necessary to detect the methylation status of the methylated marker genes, as disclosed herein. In some embodiments, the kits contain the ingredients and reagents necessary to obtain and store a biological sample from a subject.

Examples

Methylated Marker Detection by Real-Time PCR

Plasma was separated from whole blood obtained from a patient and frozen. Total nucleic acid was extracted from the plasma using magnetic bead technology and purified using the QIAsymphony platform.

The Zymo Research EZ-96 DNA methylation-Direct kit was used for bisulfite conversion of the nucleic acid. This kit is also used for clean-up and concentration of the nucleic acid following conversion.

When present, methylated Septin 9, IKZF1, and BCAT1 DNA was amplified and detected with methylation and bisulfite conversion specific primers and TaqMan probes, as depicted below, using a Viia 7 instrument (Life Technologies). Amplification and detection of beta-actin (ACTB) was used as an internal control for the presence of amplifiable DNA; the ACTB primers and probe are specific for bisulfite-converted beta-actin sequence.

[Septin 9 forward primer]
                                                          SEQ ID NO: 1
TGT TTT TCG CGC GAT TC

[Septin 9 reverse primer]
                                                          SEQ ID NO: 2
CAC CCA CCT TCG AAA TCC G

[Septin 9 probe]
                                                          SEQ ID NO: 3
FAM-CGG TTA ACG CGT AGT TGG ATG GGA TTA BHQ1

[IKZF1 forward primer]
                                                          SEQ ID NO: 4
GAC GAC GTA TTT TTT TCG TGT TTC G

[IKZF1 reverse primer]
                                                          SEQ ID NO: 5
GCG CAC CTC TCG ACC G

[IKZF1 probe]
                                                        SEQ ID NO: 6*
CY5-TTT GTA T<u>C</u>G GAG TAG <u>C</u>GA TT<u>C</u> G-BHQ2

[BCAT1 forward primer]
                                                          SEQ ID NO: 7
GTT TTT TTG TTG ATG TAA TTC GTT AGG TC

[BCAT1 reverse primer]
                                                          SEQ ID NO: 8
CAA TAC CCG AAA CGA CGA CG

[BCAT1 probe]
                                                        SEQ ID NO: 9
HEX-CGT CGC GAG AGG GTC GGT T-BHQ2

[ACTB forward primer]
                                                         SEQ ID NO: 10
GTG ATG GAG GAG GTT TAG TAA GTT

[ACTB reverse primer]
                                                         SEQ ID NO: 11
AAT TAC AAA AAC CACA AC CTA ATA AA

[ACTB Probe]
                                                        SEQ ID NO: 12
FAM-ACC ACC ACC CAA CAC ACA ATA ACA AA CACA BHQ1
*Underlined bases are LNA bases For quality control purposes, four different controls were used. For positive controls a "high positive" or "2 ng/mL," and a "low positive" or "0.2 ng/ml" control samples were generated. For each of the positive controls, enzymatically methylated human genomic DNA was spiked into pooled normal human plasma to a final concentration as indicated (either 2 ng/mL or 0.2 ng/mL). A "marker-negative" control was generated from spiking unmethylated control genomic DNA into pooled normal plasma to a concentration of 10 ng/ml. Lastly, an extraction blank control of 1×PBS was used.

What is claimed is:

1. A detection method comprising:
    a) treating DNA from a cell free biological sample obtained from a subject having or suspected of having a colorectal neoplasm with one or more reagents that convert unmethylated cytosine bases to uracil sulfonate;
    b) amplifying the treated DNA with:
        i) a primer pair specific for a Septin 9 (SEPT9) gene, wherein the primer pair specific for the SEPT9 gene comprises a first SEPT9 primer comprising SEQ ID NO: 1 and a second SEPT9 primer comprising SEQ ID NO: 2;
        ii) a primer pair specific for an Ikaros family zinc-finger 1 (IKZF1) gene, wherein the primer pair specific for the IKZF1 gene comprises a first IKZF1 primer comprising SEQ ID NO: 4 and a second IKZF1 primer comprising SEQ ID NO: 5; and
        iii) a primer pair specific for a branched-chain aminotransferase 1 (BCAT1) gene, wherein the primer pair specific for the BCAT1 gene comprises a first BCAT1 primer comprising SEQ ID NO: 7 and a second BCAT1 primer comprising SEQ ID NO: 8; and
    c) detecting, using an oligonucleotide probe specific for SEPT9 comprising SEQ ID NO: 3, an oligonucleotide probe specific for IZKF1 comprising SEQ ID NO: 6, and an oligonucleotide probe specific for BCAT1 comprising SEQ ID NO: 9, the methylation status of the SEPT9 gene the IKZF1 gene, and the BCAT1 gene in the cell free biological sample.

2. The method of claim 1 wherein the cell free biological sample is a plasma sample.

3. The method of claim 1, wherein the cell free biological sample is a stool sample or an enema wash.

4. The method of claim 1, wherein the neoplasm is a cancer.

5. The method of claim 1, wherein the neoplasm is an adenoma.

6. The method of claim 1, wherein the neoplasm is pre-cancerous.

7. The method of claim 1, wherein said subject is human.

8. The method of claim 1, wherein the cell free biological sample comprises genomic DNA.

* * * * *

SEQUENCE LISTING

<160> NUMBER OF SEQ ID NOS: 12

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1 tgttttctcgc gcgattc                                              17

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacccacctt cgaaatccg                                             19

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cggttaacgc gtagttggat gggatta                                    27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gacgacgtat tttttcgtg tttcg                                       25

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgcacctct cgaccg                                                16

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tttgtatcgg agtagcgatt cg                                         22

```
<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtttttttgt tgatgtaatt cgttaggtc                                   29

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caatacccga aacgacgacg                                             20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
cgtcgcgaga gggtcggtt                                              19

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtgatggagg aggtttagta agtt                                        24

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aattacaaaa accacaacct aataaa                                      26

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
accaccaccc aacacacaat aacaaacaca                                  30
```